US010301639B2

(12) United States Patent
Alam et al.

(10) Patent No.: US 10,301,639 B2
(45) Date of Patent: May 28, 2019

(54) **NUCLEOTIDE SEQUENCE ENCODING HOMEOBOX-LEUCINE ZIPPER PROTEIN HAT22 (HD-ZIP PROTEIN 22) FROM *CORCHORUS OLITORIUS* AND *CORCHORUS CAPSULARIS* AND METHODS OF USE**

(71) Applicants: Bangladesh Jute Research Institute, Dacca (BD); Rafia Hasina, Honolulu, HI (US)

(72) Inventors: Maqsudul Alam, Honolulu, HI (US); Mohammed Shahidul Islam, Dacca (BD); Borhan Ahmed, Dacca (BD); Mohammed Samiul Haque, Dacca (BD); Mohammed Monjurul Alam, Dacca (BD)

(73) Assignee: Bangladesh Jute Research Institute, Dacca (BD)

(*) Notice: Subject to any disclaimer, the term of this patent is extended or adjusted under 35 U.S.C. 154(b) by 0 days.

(21) Appl. No.: 14/781,243

(22) PCT Filed: Nov. 21, 2014

(86) PCT No.: PCT/US2014/066772
§ 371 (c)(1),
(2) Date: Sep. 29, 2015

(87) PCT Pub. No.: WO2015/077538
PCT Pub. Date: May 28, 2015

(65) Prior Publication Data
US 2016/0333366 A1   Nov. 17, 2016

Related U.S. Application Data

(60) Provisional application No. 61/908,444, filed on Nov. 25, 2013.

(51) Int. Cl.
*C12N 15/82* (2006.01)
*C07K 14/415* (2006.01)
(52) U.S. Cl.
CPC ........ *C12N 15/8261* (2013.01); *C07K 14/415* (2013.01); *Y02A 40/146* (2018.01)
(58) Field of Classification Search
None
See application file for complete search history.

(56) References Cited

U.S. PATENT DOCUMENTS

| 2010/0028767 A1 | 2/2010 | Inose et al. |
| 2010/0287671 A1 | 11/2010 | Harper et al. |

FOREIGN PATENT DOCUMENTS

| WO | WO-2005/001050 A2 | 1/2005 |
| WO | WO-2012/149009 A2 | 11/2012 |
| WO | WO-2012/149009 A3 | 11/2012 |
| WO | WO-2012/177418 A1 | 12/2012 |
| WO | WO-2012/177418 A8 | 12/2012 |

OTHER PUBLICATIONS

Schena et al. Structure of homeobox-leucine zipper genes suggests a model for the evolution of gene families. Proc. Natl. Acad. Sci. U.S.A. 91 (18), 8393-8397 (1994).*
Gen Bank Accession No. U09336, Dec. 9, 1994.*
Kollmer et al. Ectopic expression of different cytokinin-regulated transcription factor genes of *Arabidopsis thaliana* alters plant growth and development. J. Plant Physiol. Aug. 15, 2011;168(12):1320-7. Epub Mar. 31, 2011.*
Whisstock J.C. et al. Prediction of protein function from protein sequence and structure. Q Rev Biophys. Aug. 2003;36(3):307-40. Review.*
Brown T.A. Gene Cloning and DNA Analysis: An Introduction. Sixth Edition, John Wiley & Sons, Apr. 19, 2010, p. 133.*
Jain et al.Genome-wide analysis of intronless genes in rice and *Arabidopsis*. Funct Integr Genomics. Feb. 2008;8(1):69-78. Epub Jun. 20, 2007.*
Islam et al. Comparative genomics of two jute species and insight into fibre biogenesis. Nat Plants. Jan. 30, 2017;3:16223.*
Kaye et al. Characterization of a gene for spinach CAP160 and expression of two spinach cold-acclimation proteins in tobacco. Plant Physiol. Apr. 1998;116(4):1367-77.*
Elhiti et al. Structure and function of homodomain-leucine zipper (HD-Zip) proteins. Plant Signal Behav. Feb. 2009;4(2):86-8. Review.*
Schena et al. The HAT4 gene of *Arabidopsis* encodes a developmental regulator. Genes Dev. Mar. 1993;7(3):367-79.*

(Continued)

*Primary Examiner* — Cynthia E Collins
(74) *Attorney, Agent, or Firm* — Foley Hoag LLP (57) ABSTRACT

The present invention relates to the isolated polynucleotide encoding homeobox-leucine zipper protein HAT22 (HD-ZIP protein 22) from the plants *Corchorus olitorius* and *Corchorus capsularis* and corresponding polypeptide derived thereof. The present invention also relates to the plants having modulated expression of a nucleic acid encoding a homeobox-leucine zipper HAT22 polypeptide or a homologue thereof, which has the ability to modify, preferably to increase/enhance, the fiber length, plant height, and/or plant biomass. More specifically, the invention relates to polypeptides having homeobox-leucine zipper protein HAT22 activity, polynucleotides encoding these polypeptides, and methods of making and using these polynucleotides and polypeptides. The present invention further provides vectors, expression constructs and host cells comprising and/or consisting of the nucleotide sequences of the homeobox-leucine zipper protein HAT22 (HD-ZIP protein 22). The invention also provides methods for producing the said protein and methods for modifying the said protein in order to improve their desirable characteristics. The said protein of the invention can be used in a variety of ways, including increasing/enhancing the fiber length, height and biomass of plants and fiber yield.

15 Claims, 1 Drawing Sheet
Specification includes a Sequence Listing.

(56) References Cited

OTHER PUBLICATIONS

Schena et al. Structure of homeobox-leucine zipper genes suggests a model for the evolution of gene families. Proc Natl Acad Sci U S A. Aug. 30, 1994;91(18):8393-7.*

Falcon-Perez JM et al. Functional domain analysis of the yeast ABC transporter Ycf1p by site-directed mutagenesis. J Biol Chem. Aug. 13, 1999;274(33):23584-90.*

Lamberg A. et al. Site-directed mutagenesis of the alpha subunit of human prolyl 4-hydroxylase. Identification of three histidine residues critical for catalytic activity. J Biol Chem. Apr. 28, 1995;270(17):9926-31.*

International Preliminary Report of Patentability dated May 31, 2016 for PCT/US2014/066772.

Kollmer et al., "Funktionelle Charakterisierung von CKX7 und cytokininregulierten Transkriptionsfaktorgenen in *Arabidopsis thaliana*," Dissertation (2009).

Harris et al., "Modulation of plant growth by HD-ZIP class I and II transcription factors in response to environmental stimuli," New Phytologist, 190: 823-837 (2011).

Chan, A. et al., Ricinus Communis Homeobox Protein, Putative, mRNA: NCBI Reference Sequence: XM_002509982.1, Aug. 6, 2009.

Jena, S.N. et al., Development, Characterization and Utilization of Novel Genomic SSRs and Expressed SSRs for Genetic Analysis in Asiatic Levant Cotton (*Gossypium herbaceum* L.):*Gossypium herbaceum* Clone NBRI_B2_832 Simple Sequence Repeat Marker, mRNA Sequence: GenBank: HQ526924.1 Feb. 17, 2011.

Motamayor, JC et al., "The Genome Sequence of the Most Widely Cultivated Cacao Type and Its Use to Identify Candidate Genes Regulating Pod Color," Genome Biol., 14(6):r53 (2013).

Paterson, AH et al., "Repeated Polyploidization of Gossypium Genomes and the Evolution of Spinnable Cotton Fibres: Hypothetical Protein B456-002G137300 [Gossypium raimondii]: Genbank: KJB14683.1." Nature 492, pp. 423-427 (2012).

International Search Report completed on Mar. 13, 2015 for PCT/US2014/066772.

* cited by examiner

NUCLEOTIDE SEQUENCE ENCODING HOMEOBOX-LEUCINE ZIPPER PROTEIN HAT22 (HD-ZIP PROTEIN 22) FROM *CORCHORUS OLITORIUS* AND *CORCHORUS CAPSULARIS* AND METHODS OF USE

RELATED APPLICATIONS

This application is a 371 National Stage application of PCT/US2014/066772, filed Nov. 21, 2014, which claims the benefit of priority to U.S. Provisional Patent Application Ser. No. 61/908,444, filed Nov. 25, 2013.

SEQUENCE LISTING

The instant application contains a Sequence Listing which has been submitted via EFS-Web and is hereby incorporated by reference in its entirety. Said ASCII copy is named JGX_901_ST25.txt and is 11.6 kilobytes in size.

FIELD OF INVENTION

The present invention relates to the field of molecular biology, and a method for increasing or enhancing the fiber length, height and/or biomass of plants by modulating expression of a nucleic acid encoding homeobox-leucine zipper HAT22 polypeptide. More, particularly, the present invention provides the homeobox-leucine zipper protein HAT22 homologues isolated from two species of jute plants, namely, *Corchorus olitorius* ("*C. olitorius*") and *Corchorus capsularis* ("*C. capsularis*"), and their application for increasing fiber length, plant height and/or plant biomass in jute by regulating expression of genes encoding homeobox-leucine zipper protein HAT22.

BACKGROUND OF THE INVENTION

Commercially cultivated jute is mainly produced from two species, namely, *Corchorus olitorius* (commonly called "tossa jute") and *Corchorus capsularis* (commonly called "white jute"). Both species are diploid (2n=14), and only two of which are used in agriculture. These two species constitute an important cash crop for the South East Asian countries and for Brazil, providing biodegradable lignocellulose fiber. Fibers are commonly used as packaging materials for industrial products, and for production of other value-added products, such as yarns and textiles, ropes, twines and nets, non-woven fabrics, tissues, pulp and paper, geotextiles, composites and home textiles. Due to the environment-friendly and biodegradable characteristics of jute fiber, demand is increasing in the world market. In order to keep up with rising global demand, further improvement of jute fiber production is necessary. Jute fibers obtained from the bark of the stem and fibers are grouped into bundles. Fibers arranged as triangular wedges of sclerenchymatous fiber cells alternate with medullary rays of other soft tissue. These fiber cells differentiate from phloem and develop in four chronological stages—initiation, elongation, secondary cell wall thickening, and maturation stages. Little is known about the genetic control of jute fiber initiation and elongation. However, fiber length and uniformity are common requirements for most industrial uses. For example, long fiber and uniform cell are ideal for the production of fine fabrics for the textile industry. In the pulp industry, strength characteristics of pulp are determined in part by fiber length, pulp yield and alkali consumption, due to their strength and bonding properties. In order to meet industrial needs, the development of jute varieties with desirable fiber length as well as strength is necessary. Therefore, the biosynthesis of fiber and the molecular biology involved in fiber biosynthesis are of significant importance.

Bast fiber primarily begins from the apical meristem and, gradually, the fiber elongates, mostly through intrusive growth, until the onset of secondary wall development. Fiber cell elongation is a process which results from the interaction between internal turgor pressure and the mechanical strength of the cell wall, which is controlled endogenously. However, the mechanism and genes involved in fiber cell elongation have not been totally determined. Several candidate genes associated with the elongation and formation of cotton fibers have been identified. For example, five genes from cotton plants which are specially expressed at the cotton fiber elongation stage were identified by differential screening and display methods [U.S. Pat. Nos. 5,880,100 and 5,932,713, 6,225,536 and 6,166,294; all of which are incorporated by reference], but there is no such report in area of the jute and/or bast fiber initiation and elongation.

Homeobox-leucine zipper (HD-Zip) proteins are transcription factors unique to plants which are encoded by multiple copies of the genes in a plant genome. For example, *Arabidopsis thaliana* genome has more than 25 genes of this family. Among the genes, homeobox-leucine zipper protein HAT22 (HD-ZIP protein 22) is involved in the elongation of the vascular fiber cell.

HD-ZIP protein 22 is expressed in the interfascicular regions in which fibers differentiate, which is consistent with its role in the control of interfascicular fiber differentiation. Furthermore, it is also expressed in phloem during phases of secondary growth (Tornero et al. 1996), indicating its possible role in the regulation of vascular tissue formation (Zhong and Ye, 1999). Unlike other plant homeobox genes, HD-ZIP protein 22 is not expressed in meristems, and the function of HD-ZIP protein 22 is likely to participate in the regulation of the identity and/or activity of phloem tissues during secondary phases of vascular development (Tornero et al. 1996).

In view of the fact that Homeobox-leucine zipper protein HAT22 may play an important role in the spatial control of phloem fiber differentiation, it is desirable to take a genetic approach to understanding the biosynthesis of fiber in the plant by exploring and utilizing molecular biological and genetic information regarding homeobox-leucine zipper protein HAT22. Besides, because the fiber biosynthesis pathway and genetic make-up of each species of plant typically varies, a species-specific approach is also preferable in order to optimize yield of fiber from jute plants, and obtain compatible results to enable use in industry.

SUMMARY OF THE INVENTION

The invention, in certain embodiments, relates to polynucleotides and polypeptides involved in determining or shaping fiber length, plant height, and/or plant biomass, and methods of using the same.

The present invention also relates to identification of genes involved in homeobox-leucine zipper protein HAT22-mediated processes, and the use of such genes and proteins for altering characteristics in plants.

The present invention provides homeobox-leucine zipper proteins HAT22 derived from two jute plants, *C. olitorius* and *C. capsularis*, the method comprising and/or consisting of modulating the expression of a homeobox-leucine zipper HAT22 polypeptide in a plant cell, and a method for modulating the enhanced fiber length and/or height and/or biomass in a plant.

One aspect of the present invention is to provide genes encoding proteins, derived from C. olitorius and C. capsularis, which are involved in enhanced fiber length, plant height, and/or plant biomass production, and have a homeobox-leucine zipper protein HAT22-like sequence. More specifically, the present invention provides a gene capable of inducing and/or enhancing fiber length, plant height, and/or plant biomass production in a plant; and a protein encoded thereby, and uses thereof.

Another object of the present invention is to provide genetic information regarding homeobox-leucine zipper protein HAT22 to be exploited/utilised for inducing, improving, or enhancing the production of fiber length and/or plant height and/or/biomass in the plants of C. olitorius and C. capsularis, as well as in other bast fiber producing plants. Still another object of the present invention is to obtain transgenic plants of C. olitorius and C. capsularis with enhanced fiber length and/or plant height/biomass by regulating the biosynthesis of homeobox-leucine zipper protein HAT22 in the plant.

Yet another object of the present invention is to provide isolated polynucleotides, which may be useful to facilitate performance of methods disclosed herein and development of transgenic C. olitorius and C. capsularis plants.

Further object of the present invention is to provide a commercially feasible way to increasing fiber length and/or plant height for jute fiber based products.

The present invention further provides a gene isolated from C. olitorius encoding a protein that has the amino acid sequence as set forth in SEQ ID NO: 3, which is involved in inducing, improving, or enhancing fiber length and/or plant height and/or biomass, and has a homeobox-leucine zipper protein HAT22-like sequence. The present invention also provides a gene encoding a protein that has an amino acid sequence modified by the addition or deletion of one or a plurality of amino acids and/or replacement with other amino acids in the amino acid sequence as set forth in SEQ ID NO: 3, which is involved in inducing, improving, or enhancing the fiber length and/or plant height/biomass, and has a homeobox-leucine zipper protein HAT22-like sequence. The present invention additionally provides a gene that hybridizes the nucleic acid as set forth in SEQ ID NO: 1, specifically its DNA or a portion thereof, and that encodes a protein that is involved in inducing, improving, or enhancing the fiber length and/or plant height/biomass and has a homeobox-leucine zipper protein HAT22-like sequence.

The present invention furthermore provides a gene isolated from C. capsularis encoding a protein that has the amino acid sequence as set forth in SEQ ID NO: 6, which is involved in inducing, improving, or enhancing fiber length and/or plant height/biomass, and has a homeobox-leucine zipper protein HAT22-like sequence. The present invention also provides a gene encoding a protein that has an amino acid sequence modified by the addition or deletion of one or a plurality of amino acids and/or replacement with other amino acids in the amino acid sequence as set forth in SEQ ID NO: 6, which is involved in inducing, improving, or enhancing the fiber length and/or plant height/biomass, and has a homeobox-leucine zipper protein HAT22-like sequence. The present invention further provides a gene that hybridizes to the nucleic acid as set forth in SEQ ID NO: 4, specifically its DNA or a portion thereof, and that encodes a protein which is involved in inducing, improving, or enhancing the fiber length and/or plant height/biomass and has a homeobox-leucine zipper protein HAT22-like sequence.

According to one embodiment of the present invention, the plant of C. olitorius is variety O-4, and the plant of C. capsularis is variety CVL-1.

Another embodiment of the present invention discloses a recombinant gene construct comprising and/or consisting of a polynucleotide having nucleotide sequence set forth in SEQ ID NO: 2 and/or SEQ ID NO: 5, wherein the polynucleotide is expressible in a host cell to produce a homologue of homeobox-leucine zipper protein HAT22 in the plants of C. olitorius and C. capsularis, respectively.

Further embodiments of the present invention are a transformant comprising and/or consisting of a recombinant gene construct capable of expressing a polynucleotide having nucleotide sequence set forth in SEQ ID NO: 2 and/or SEQ ID NO: 5 to produce homologue of homeobox-leucine zipper HAT22 protein.

The present invention also provides a method for producing a protein involved in inducing, improving, or enhancing fiber length and/or plant height/biomass, and has a homeobox-leucine zipper protein HAT22-like sequence by culturing and/or cultivating the above host. The present invention also provides a method for inducing, improving, or enhancing fiber length and/or plant height/biomass of plants or plant cells. Furthermore also disclosed is a method comprising and/or consisting of introducing the above gene into plants or plant cells, and driving the expression of the said genes.

One skilled in the art will readily appreciate that the present invention is well adapted to carry out the objects and obtain the ends and advantages mentioned, as well as those inherent therein. The embodiments described herein are not intended as limitations on the scope of the invention.

These and other features, aspects, and advantages of the present invention will become better understood with reference to the following description and claims.

DETAILED DESCRIPTION OF THE INVENTION

Figure 1:
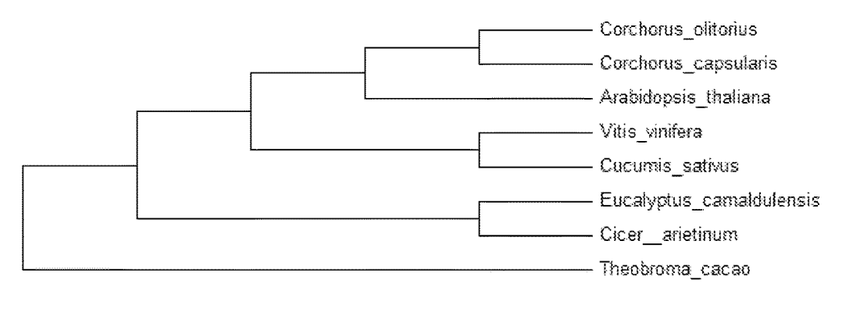
FIG. 1 shows the phylogenetic tree comparing SEQ ID NO. 3 from C. olitorius and SEQ ID NO. 6 from C. capsularis with other amino acid sequences, which produce homeobox-leucine zipper HAT22 proteins.

The invention can be more fully understood from the following detailed description and the accompanying drawing which form a part of this application.

The definitions and/or methods provided herein define the present invention and guide those of ordinary skill in the art in the practice of the present invention. Except where otherwise stated, terms are to be understood according to conventional usage by those of ordinary skill in the relevant art. To the extent to which any of the definitions and/or methods is found to be inconsistent with any of the definitions and/or methods provided in any patent or non-patent reference incorporated herein or in any reference found elsewhere, it is understood that the said definition and/or method which has been expressly provided/adopted in this application will be used herein. The singular terms "a," "an," and "the" include plural referents unless context clearly indicates otherwise. Similarly, the word "or" is intended to include "and" unless the context clearly indicates otherwise.

Hence, "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below.

The present invention includes isolated polynucleotides encoding homeobox-leucine zipper proteins HAT22 extracted from C. olitorius and C. capsularis, and corresponding polypeptides derived thereof. More particularly, the present invention provides homeobox-leucine zipper protein HAT22 homologues and their application in inducing, improving, or enhancing fiber length and/or plant height/biomass in C. olitorius and C. capsularis, as well as transgenic C. olitorius and C. capsularis plant thereof. The genomic sequences of the invention that encode the enzymes were identified primarily by comparison of nucleotide sequences of C. olitorius and C. capsularis genomic DNA with the nucleotide sequences of known enzyme genes of other plants. Prior to this invention, the nucleotide sequences of the C. olitorius and C. capsularis genes, the reading frames, the positions of exons and introns, the structure of the enzymes, and their potential usefulness in the development of high fiber quality were not known, particularly in respect of fiber length, plant height/biomasss and yield potential of jute plants.

Analysis of the genome sequences of commercially cultivated jute species, C. olitorius and C. capsularis, revealed that both species have a single gene coding for enzymes with catalytic activities in inducing, improving, or enhancing fiber length and/or plant height in jute. The nucleotide sequences were initially annotated by software programs, such as Augustus, Semi-HMM-based Nucleic Acid Parser (SNAP), and Geneid (Genome BioInformatics Research Lab), which can identify putative coding regions, introns, and splice junctions. Further automated and manual curation of the nucleotide sequences was performed to refine and establish precise characterization of the coding regions and other gene features.

Over 30,096 cDNAs from C. olitorius and 37,031 cDNA from C. capsularis were partially or fully sequenced. From them we developed a single cDNA from each species encoding new enzymes, with putative roles, preferred catalytic activities in inducing, improving, or enhancing the fiber length and/or plant height in jute.

Open reading frames (ORFs) were analyzed following full or partial sequencing of clones of cDNA libraries derived from C. olitorius and C. capsularis mRNAs, and were further analyzed using sequence analysis software, and by determining homology to known sequences in databases (public/private).

In the context of this disclosure, a number of terms used throughout the specification have the indicated meanings unless expressly indicated to have a different meaning.

As used herein, a "polynucleotide" is a nucleotide sequence such as a nucleic acid fragment.

A polynucleotide may be a polymer of RNA or DNA that is single- or double-stranded, that optionally contains synthetic, non-natural or altered nucleotide bases. A polynucleotide in the form of a polymer of DNA may comprise and/or consist of one or more segments of cDNA, genomic DNA, synthetic DNA, or mixtures/combination thereof. An isolated polynucleotide of the present invention may include at least one of 150 contiguous nucleotides (both upstream and downstream) derived from SEQ ID No. 1 and, SEQ ID No. 4, or the complement of such sequences.

"Polypeptide" as used herein, is a single linear chain of amino acids bonded together by peptide bonds, and having usually a sequence greater than 100 amino acids in length. "Isolated" means altered "by the hand of man" from the natural state. If a composition or substance occurs in nature, it has been "isolated" if it has been changed or removed from its original environment, or both. For example, a polynucleotide or a polypeptide naturally present in a living plant or animal is not "isolated," but the same polynucleotide or polypeptide separated from the coexisting materials of its natural state is "isolated", as the term is employed herein.

The term "gene", as used herein, is defined as the genomic sequences of the plant C. olitorius and C. capsularis, particularly polynucleotide sequence encoding polypeptide sequence of the homeobox-leucine zipper HAT22 enzymes involved in the preferred catalytic activities in enhancing fiber length and/or plant height in jute. The term can further include nucleic acid molecules comprising upstream, downstream, and/or intron nucleotide sequences. A "coding sequence" or "coding region" refers to a nucleic acid molecule having sequence information necessary to produce a gene product, such as an amino acid or polypeptide, when the sequence is expressed. The coding sequence may comprise and/or consist of untranslated sequences (including introns or 5' or 3' untranslated regions) within translated regions, or may lack such intervening untranslated sequences (e.g., as in cDNA).

The term "oligonucleotide", as used herein, is a short polynucleotide or a portion of polynucleotide which may preferably comprise 10-1000, most preferably 12 to 50 nucleotides in length. In respect to the embodiment of the present invention, nucleotides contained within the oligonucleotides can be analogs or derivatives of naturally occurring nucleotides.

The term "primer", as used herein, is an oligonucleotide capable of binding to a target nucleic acid sequence and priming the nucleic acid synthesis. An amplification oligonucleotide as defined herein may preferably be 10 to 50, most preferably 15 to 25 nucleotides in length. Furthermore, the amplification oligonucleotides of the present invention may be chemically synthesized and such oligonucleotides are not naturally occurring nucleic acids.

The abbreviation used throughout the specification to refer to nucleic acids comprising and/or consisting of nucleotide sequences are the conventional one-letter abbreviations. Thus when included in a nucleic acid, the naturally occurring encoding nucleotides are abbreviated as follows: adenine (A), guanine (G), cytosine (C), thymine (T) and uracil (U). Also, unless otherwise specified, the nucleic acid sequences presented herein is the 5'→3' direction.

As used herein, the term "complementary" and derivatives thereof are used in reference to pairing of nucleic acids by the well-known rules that A pairs with T or U and C pairs with G. Complement can be "partial" or "complete". In partial complement, only some of the nucleic acid bases are matched according to the base pairing rules; while in complete or total complement, all the bases are matched according to the pairing rule. The degree of complement between the nucleic acid strands may have significant effects on the efficiency and strength of hybridization between nucleic acid strands as well known in the art. The efficiency and strength of said hybridization depends upon the detection method.

The term "host cell", as used herein, includes any cell type which is susceptible to transformation, transfection, transduction, expression and the like with a nucleic acid construct or expression vector comprising and/or consisting of a polynucleotide of the present invention. Suitable host cell includes fungi and/or plant cells, especially bast fiber producing plant cells.

The term "operably linked" generally denotes herein a configuration in which a control sequence is placed at an appropriate position relative to the coding sequence of the polynucleotide sequence such that the control sequence directs the expression of the coding sequence of a polypeptide. For example, a promoter can be operably-linked with a coding sequence when it affects the expression of that coding sequence, i.e. that the coding sequence is under the transcriptional control of the promoter.

A "vector" generally refers to a replicon, such as plasmid, phage, cosmid, yeast or virus to which another nucleic acid segment may be operably inserted so as to bring about the replication or expression of the segment. The term "vector" is also intended to refer to a nucleic acid molecule capable of transporting another nucleic acid to which it has been linked. One type of vector is a "plasmid," which refers to a circular double-stranded DNA loop into which additional DNA segments may be ligated. Another type of vector is a viral vector, where additional DNA segments may be ligated into the viral genome. Certain vectors are capable of autonomous replication in a host cell into which they are introduced (e.g., bacterial vectors having a bacterial origin of replication and episomal mammalian vectors). Other vectors can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "nucleic acid construct" or "DNA construct" is sometimes used to refer to a coding sequence or sequences operably linked to appropriate regulatory sequences and inserted into a vector for transforming a cell. This term may be used interchangeably with the term "transforming DNA" or "transgene."

The term "promoter", as used herein, refers to a nucleic acid sequence that functions to direct transcription of a downstream gene. The promoter will generally be appropriate to the host cell in which the target gene is being expressed. The promoter together with other transcriptional and translational regulatory nucleic acid sequences (also termed "control sequences") is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

As used herein, "homeobox-leucine zipper HAT22 polypeptide" means a polypeptide having homeobox-leucine zipper HAT22 activity, i.e., involved in inducing, improving, or enhancing fiber length and/or plant height/biomass in plants. Homeobox-leucine zipper protein HAT22 activity stimulates fiber cell growth and/or plant height/biomass. DNA-binding properties of the homeobox-leucine zipper protein HAT22 showed that they interact with DNA as homodimers and recognize two distinct 9 bp (approximately) pseudopalindromic sequences, CAAT(G/C)ATTG, as determined by selecting high-affinity binding sites from random-sequence DNA. The term is also inclusive of fragments, variants, and homologues, with any one of the above stated functions.

The term "homologues", as used herein, refers to a protein encompass peptides, oligopeptides, polypeptides, proteins and enzymes having amino acid substitutions, deletions and/or insertions relative to the unmodified protein in question and having similar biological and functional activity as the unmodified protein from which they are derived.

A deletion refers to removal of one or more amino acids from a protein.

An insertion refers to one or more amino acid residues being introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues.

A substitution refers to replacement of amino acids of the protein with other amino acids having similar properties (such as similar hydrophobicity, hydrophilicity, antigenicity, propensity to form or break α-helical structures or β-sheet structures). Amino acid substitutions are typically of single residues, but may be clustered depending upon functional constraints placed upon the polypeptide and may range from 1 to 10 amino acids; insertions will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company (Eds) and Table 1 below).

TABLE 1

Examples of conserved amino acid substitutions

| Residue | Conservative Substitutions |
| --- | --- |
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Amino acid substitutions, deletions and/or insertions may readily be made using peptide synthetic techniques well known in the art, such as solid phase peptide synthesis and/or any other synthetic techniques, or by recombinant DNA manipulation. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), Quick Change Site Directed mutagenesis (Stratagene, San Diego, Calif.), PCR-mediated site-directed mutagenesis or other site-directed mutagenesis protocols.

As used herein, a "biologically active portion" may refer to a fragment of homeobox-leucine zipper HAT22 protein having a biological activity for catalyzing the initiation, formation, enhancement, or variation in the composition of phloem fiber in the plant of *C. olitorius* or *C. capsularis*. Biologically active portions of a homeobox-leucine zipper HAT22 protein include peptides or polypeptides comprising amino acid sequences sufficiently identical to or derived from the amino acid sequence of the homeobox-leucine zipper HAT22 protein, e.g., the amino acid sequence as set forth in SEQ ID NO: 3 or SEQ ID NO: 6, which include fewer amino acids than the full length homeobox-leucine zipper HAT22 protein, and exhibit at least one activity of a homeobox-leucine zipper HAT22 protein. Typically, biologically active portions comprise a domain or motif with at least one activity of the homeobox-leucine zipper HAT22 protein. A biologically active portion of a homeobox-leucine zipper HAT22 protein can be a polypeptide which is, for example, 254, 255, 256, 257, 258, 259, 260, 261, 262, 263, 264, 265, 266, or 267, amino acids in length.

The homeobox-leucine zipper HAT22 protein may have an amino acid sequence set forth in SEQ ID NO: 3 or SEQ ID NO: 6. In other embodiments, the homeobox-leucine zipper HAT22 protein is substantially identical to SEQ ID NO: 3 or SEQ ID NO: 6, and retains the functional activity of the protein of SEQ ID NO: 3 or SEQ ID NO: 6, yet differs in amino acid sequence due to natural allelic variation or mutagenesis. In another embodiment, the homeobox-leucine zipper HAT22 protein comprises an amino acid sequence at least about 95%, 96%, 97%, 98%, 99%, 99.1%, 99.2%, 99.3%, 99.4%, 99.5%, 99.6%, 99.7%, 99.8%, 99.9% or more identical to SEQ ID NO: 3 or SEQ ID NO: 6.

The term "domain", as used herein, refers to a set of amino acids conserved at specific positions along an alignment of sequences of evolutionarily related proteins. While amino acids at other positions can vary between homologues, amino acids that are highly conserved at specific positions indicate amino acids which are likely to be essential in the structure, stability or function of a protein. Identified by their high degree of conservation in aligned sequences of a family of protein homologues, they can be used as identifiers to determine if any polypeptide in question belongs to a previously identified polypeptide family.

The term "motif", as used herein, refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: The Proteomics Server for In-Depth Protein Knowledge and Analysis, Nucleic Acids Res. 31:3784-3788(2003)). Domains or motifs may also be identified using routine techniques, such as by sequence alignment.

For the purposes of the invention, "transgenic", "transgene" or "recombinant" means with regard to, for example, a nucleic acid sequence, an expression cassette, gene construct or a vector comprising and/or consisting of the nucleic acid sequence or an organism transformed with the nucleic acid sequences, expression cassettes or vectors according to the invention, all those constructions brought about by recombinant methods in which: (a) the nucleic acid sequences encoding proteins useful in the methods of the invention, or (b) genetic control sequence(s) which is operably linked with the nucleic acid sequence according to the invention, for example a promoter, or (c) a) and b) are not located in their natural genetic environment or have been modified by recombinant methods. The modification may take the form of, for example, a substitution, addition, deletion, inversion or insertion of one or more nucleotide residues. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of about 50 bp, preferably of about 500 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815 (both of which are incorporated by reference).

A transgenic plant for the purposes of the invention is understood to include those plants in which the nucleic acids used in the method of the invention are not at their natural locus in the genome of the plant, and thus it is possible for the nucleic acids to be expressed homologously or heterologously. However, transgenic also means that, while the nucleic acids according to the invention or used in the inventive method are at their natural position in the genome of a plant, the sequence has been modified with regard to the natural sequence, and/or that the regulatory sequences of the natural sequences have been modified. Transgenic is understood as meaning the expression of the nucleic acids according to the invention at an unnatural locus in the genome, where homologous or, preferably, heterologous expression of the nucleic acids takes place.

The term "introduction" or "transformation", as used herein, refers to herein encompass the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation.

Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation and chemicals which increase free DNA uptake, injection of the DNA directly into the plant, particle gun bombardment, and transformation using viruses or pollen and microprojection. Transgenic plants, including transgenic crop plants, are preferably produced via Agrobacterium-mediated transformation. An advantageous transformation method is the transformation in planta (Sajib et. al. 2008).

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organization. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants may be selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The term "increased expression" or "overexpression" as used herein refers to any form of expression that is additional to the original wild-type expression level.

Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the polypeptide of interest. For example, endogenous promoters may be altered in vivo by mutation, deletion, and/or substitution (see, Kmiec, U.S. Pat. No. 5,565,350 (incorporated by reference); Zarling et al., WO 93/22443 (incorporated by reference)), or isolated promoters may be introduced into a plant cell in the proper orientation and distance from a gene of the present invention so as to control the expression of the gene.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) or the coding sequence of the partial coding sequence to increase the amount of the mature message that accumulates in the cytosol. Inclusion of a splice able intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994).

To determine the percent identity of two amino acid sequences or of two nucleic acid sequences, the sequences can be aligned for optimal comparison purposes (e.g., gaps can be introduced in one or both of a first and a second amino acid or nucleic acid sequence for optimal alignment and non-identical sequences can be disregarded for comparison purposes). The length of a reference sequence aligned for comparison purposes can be at least 95% of the length of the reference sequence. The amino acid residues or nucleotides at corresponding amino acid positions or nucleotide positions can then be compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In one embodiment, the percent identity between two amino acid sequences can be determined using the Needleman and Wunsch (J. Mol. Biol. 48:444-453 (1970)) algorithm which has been incorporated into the GAP program in the GCG software package (available at http://www.gcg.com), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences can be determined using the algorithm of E. Meyers and W. Miller (Comput. Appl. Biosci. 4:11-17 (1988)) which has been incorporated into the ALIGN program (version 2.0 or 2.0U), using a PAM120 weight residue table, a gap length penalty of 12 and a gap penalty of 4.

Exemplary computer programs which can be used to determine identity between two sequences include, but are not limited to, the suite of BLAST programs, e.g., BLASTN, BLASTX, and TBLASTX, BLASTP and TBLASTN, publicly accessible at www.ncbi.nlm.nih.gov/BLAST.

Sequence searches are typically carried out using the BLASTN program, when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases.

An alignment of selected sequences in order to determine "% identity" between two or more sequences is performed using for example, the CLUSTAL-W program.

One embodiment of the present invention is an isolated polynucleotide encoding homeobox-leucine zipper HAT22 polypeptide found in *C. olitorius* and *C. capsularis* comprising and/or consisting of nucleotide sequence as set forth in SEQ ID NO 2 and SEQ ID NO 5, respectively. Correspondingly, the respective homeobox-leucine zipper HAT22 polypeptide encoded by these nucleotide sequences shall possess amino acid sequence as set forth in SEQ ID NO 3 and SEQ ID NO 6. According to one embodiment of the invention, SEQ ID NO 3 refers to the polypeptide sequence of the *C. olitorius*-derived homeobox-leucine zipper protein HAT22 homologue, and SEQ ID NO 6 refers to the polypeptide sequence of the *C. capsularis*-derived homeobox-leucine zipper protein HAT22 homologue. Both these enzymes are present in the biosynthesis pathway of fiber in *C. olitorius* and *C. capsularis* for catalyzing the enhancing fiber length, plant height, and/or plant biomass production in the plant.

The present invention also provides a gene sequence encoding homeobox-leucine zipper protein HAT22 homologues from the plants *C. olitorius* and *C. capsularis*.

In one embodiment, the 1296 by long polynucleotide illustrated in SEQ ID No. 1 is the full length gene isolated from *C. olitorius*. This gene sequence includes at least 150 contiguous nucleotides from both upstream and downstream of the gene. This also provides the intronic sequence of the gene.

In another embodiment, the 1337 by long polynucleotide illustrated in SEQ ID No. 4 is the full length gene isolated from *C. capsularis*. This gene sequence includes at least 150 contiguous nucleotides from both upstream and downstream of the gene. This also provides the intronic sequence of the gene.

In still another embodiment of the present invention, an isolated polynucleotide encoding a polypeptide comprising and/or consisting of nucleotide sequence set forth in SEQ ID NO 2 and/or SEQ ID NO 5 is provided. SEQ ID NO 2 refers to the polynucleotide sequence of the *C. olitorius*-derived homeobox-leucine zipper HAT22 protein homologue sequence and SEQ ID NO 5 refers to the polynucleotide sequence of the *C. capsularis*-derived homeobox-leucine zipper HAT22 protein homologue sequence.

In still another embodiment, an isolated nucleic acid molecule which is capable of encoding a homeobox-leucine zipper HAT22 polypeptide, or biologically active fragment thereof, comprises a nucleotide sequence which is at least about 95%, 96%, 97%, 98%, 99%, 99.1%, 99.2%, 99.3%, 99.4%, 99.5%, 99.6%, 99.7%, 99.8%, 99.9% or more identical to the entire length of the nucleotide sequence set forth in SEQ ID NO: 2, SEQ ID NO: 5, or any complement thereof.

In one embodiment, the 804 by long polynucleotide illustrated in SEQ ID No. 2 is the full length cDNA clone encoded homeobox-leucine zipper HAT22 protein exhibiting an open reading frame encoding a 267 amino acid polypeptide, as in SEQ ID No. 3, with a calculated molecular mass of about 29.99 kD. Through SMART analysis of SEQ ID No. 3, it reveals presence of homeobox domain in the sequence. This is a DNA-binding factor, which is involved in the transcriptional regulation of key developmental processes of plant. This is homeobox-leucine zipper HAT22 protein involved in the enhancing fiber length, plant height, and/or plant biomass production in the plant.

In one embodiment, the 807 by long polynucleotide illustrated in SEQ ID No. 5 is the full length cDNA clone encoded homeobox-leucine zipper HAT22 protein exhibiting an open reading frame encoding a 268 amino acid polypeptide, as in SEQ ID No. 6, with a calculated molecular mass of about 30.10 kD. Through SMART analysis of SEQ ID No. 6, it reveals presence of homeobox domain in the sequence. This is a DNA-binding factor, which is involved in the transcriptional regulation of key developmental processes of plant. This is homeobox-leucine zipper HAT22 protein involved in the enhancing fiber length, plant height, and/or plant biomass production in the plant.

In accordance with an embodiment of the present invention, the isolated polynucleotide illustrated in SEQ ID NO 2 can be obtained by PCR amplification of the conserved region of the gene using total RNA isolated from the plant of *C. olitorius*, and SEQ ID NO 5 can be obtained by PCR amplification of the conserved region of this gene using total RNA isolated from the plant of *C. capsularis*. As set forth in the preceding description, the plant of *C. olitorius* applied is variety 0-4, and *C. capsularis* applied is variety CVL-1.

Another embodiment of the present invention, a recombinant gene construct comprising and/or consisting of a polynucleotide having nucleotide sequence set forth in SEQ ID NO 2 and/or SEQ ID NO 4 is disclosed, wherein the polynucleotide is expressible in a host cell, and is translatable to produce homologue of homeobox-leucine zipper HAT22 protein in the plant of *C. olitorius* and *C. capsularis*. The procedure for amplifying, cloning and sequencing the homeobox-leucine zipper HAT22 from the plant of *C. olitorius* and *C. capsularis* is further detailed in Example 2. In certain embodiments, the recombinant gene construct further comprises a promoter region operably-linked to enhance expression of the polynucleotide template. Under the transcriptional control of the specific promoter, the expression of the coding region within the recombinant gene constructs containing polynucleotide of SEQ ID NO 2 and/or SEQ ID NO 4 can then be enhanced, leading to higher yield of the homeobox-leucine zipper HAT22 protein.

According to a feature of the invention, the modulated expression is increased expression or activity, e.g. overexpression of a homeobox-leucine zipper HAT22 polypeptide encoding nucleic acid molecule, e.g. of a nucleic acid molecule encoding SEQ ID NO 2 and SEQ ID NO 5. Methods for increasing expression of nucleic acids or genes, or gene products, are well documented in the art and examples are provided in the definitions section.

The invention also provides a method for the production of transgenic plants having enhanced fiber length and yield relative to control plants, comprising and/or consisting of introduction and expression in a plant of any nucleic acid encoding a homeobox-leucine zipper HAT22 polypeptide as defined herein above.

More specifically, the present invention provides a method for the production of transgenic plants having enhanced fiber yield in comparison to the null control plants, which method comprises:

(i) introducing and expressing in a plant or plant cell a homeobox-leucine zipper HAT22 polypeptide-encoding nucleic acid or a genetic construct comprising and/or consisting of a homeobox-leucine zipper HAT22 polypeptide-encoding nucleic acid; and (ii) cultivating the plant cell under conditions promoting fiber cell growth and development. Another aspect of the invention relates to an isolated polynucleotide which encodes a homeobox-leucine zipper HAT22 protein and is derived from the plant C. olitorius, comprising a nucleic acid molecule selected from the group consisting of:

a) a nucleic acid molecule comprising the nucleotide sequence set forth in SEQ ID NO: 2, or a complement thereof; and b) a nucleic acid molecule comprising a nucleotide sequence having at least 95% sequence identity to the nucleotide sequence set forth in SEQ ID NO: 2, or a complement thereof.

In certain embodiments, the plant of C. olitorius is variety O-4.

Another aspect of the invention relates to an isolated polynucleotide which encodes a homeobox-leucine zipper HAT22 protein and is derived from the plant C. capsularis, comprising a nucleic acid molecule selected from the group consisting of:

a) a nucleic acid molecule comprising a nucleotide sequence set forth in SEQ ID NO: 5, or a complement thereof; and b) a nucleic acid molecule comprising a nucleotide sequence having at least 95% sequence identity to the nucleotide sequence set forth in SEQ ID NO: 5, or a complement thereof.

In certain embodiments, the plant of C. capsularis is variety CVL-1.

Another aspect of the invention relates to an isolated homeobox-leucine zipper HAT22 polypeptide comprising an amino acid sequence as set forth in SEQ ID NO: 3, or a biologically-active fragment, thereof, said polypeptide comprises one or more functions selected from the group consisting of catalyzing the initiation, formation, improvement, enhancement, and variation, to thereby modify the fiber length, plant height, biomass, or any combination thereof in the plant of C. olitorius.

In certain embodiments, the plant of C. olitorius is variety O-4.

In certain embodiments, said polypeptide comprises at least 95% sequence identity to the amino acid sequence set forth in SEQ ID NO: 3.

Another aspect of the invention relates to an isolated homeobox-leucine zipper HAT22 protein polypeptide comprising an amino acid sequence as set forth in SEQ ID NO: 6, or biologically active fragment thereof, said polypeptide comprises one or more functions selected from the group consisting of catalyzing the initiation, formation, improvement, enhancement, and variation, to thereby modify the fiber length, plant height, biomass, or any combination thereof in the plant of C. capsularis.

In certain embodiments, the plant of C. capsularis is variety CVL-1.

In certain embodiments, said polypeptide comprises at least 95% sequence identity to the amino acid sequence set forth in SEQ ID NO: 6.

Another aspect of the invention relates to a recombinant gene construct comprising a polynucleotide selected from the group consisting of:

a) a nucleic acid molecule comprising a nucleotide sequence set forth in SEQ ID NO: 2 or SEQ ID NO: 5, or a complement thereof; and b) a nucleic acid molecule comprising a nucleotide sequence having at least 95% sequence identity to the nucleotide sequence set forth in SEQ ID NO: 2 or SEQ ID NO: 5, or a complement thereof; wherein the polynucleotide is expressible in a host cell to produce a homologue of homeobox-leucine zipper HAT22 polypeptide in the plants of C. olitorius and C. capsularis.

In certain embodiments, the recombinant gene construct further comprises a promoter region operably-linked to a nucleic acid molecule set forth in a) or b), wherein said promoter enhances the transcription or expression of the polynucleotide.

Another aspect of the invention relates to a transformant comprising a recombinant gene construct capable of expressing a polynucleotide selected from the group consisting of:

a) a nucleic acid molecule comprising a nucleotide sequence set forth in SEQ ID NO: 2 or SEQ ID NO: 5, or a complement thereof; and b) a nucleic acid molecule comprising a nucleotide sequence having at least 95% sequence identity to the nucleotide sequence set forth in SEQ ID NO: 2 or SEQ ID NO: 5, or a complement thereof; wherein said transformant produces a homologue of homeobox-leucine zipper HAT22 polypeptide.

Another aspect of the invention relates to a method for producing a plant or transgenic plant comprising one or more characteristics selected from the group consisting of increased, enhanced, or modified fiber yield, fiber length, and plant height, relative to control plants, the method comprising the steps of:

a) introducing into a plant cell a recombinant gene construct comprising a polynucleotide selected from the group consisting of: i) a nucleic acid molecule comprising a nucleotide sequence set forth in SEQ ID NO: 2 or SEQ ID NO: 5, or a complement thereof; and ii) a nucleic acid molecule comprising a nucleotide sequence having at least 95% sequence identity to the nucleotide sequence set forth in SEQ ID NO: 2 or SEQ ID NO: 5, or a complement thereof; and b) expressing a polypeptide selected from the group consisting of: i) a polypeptide comprising an amino acid sequence set forth in SEQ ID: NO: 3 or SEQ ID NO: 6, or a biologically-active fragment thereof; and ii) a polypeptide having at least 95% sequence identity to the amino acid sequence set forth in SEQ ID NO: 3 or SEQ ID NO: 6; and c) cultivating the plant cell under conditions for promoting plant growth and development.

The sequences provided by the present invention can also be used as preparatory materials for the rational modification or design of novel enzymes with characteristics that enable the enzymes to perform better in demanding processes.

The present disclosure includes as contained in the appended claims, as well as that of the foregoing description. Although this invention has been described in its preferred form with a degree of particularity, it is understood that the present disclosure of the preferred form has been made only by way of example and that numerous changes in the details of construction and the combination and arrangements of parts may be resorted to without departing from the scope of the invention and claims.

Various references are cited herein, the disclosures of which are incorporated by reference in their entireties.

EXAMPLES

The following example is intended to further illustrate the invention, without any intent for the invention to be limited to the specific embodiments described therein.

Example 1 Designing and Synthesis of Primers

The primers used in the study were either designed from the manually curated transcriptome and the invention to be limited to the specific embodiments des C. olitorius and C. capsularis, by choosing the sequences manually with complete ORFs or using databases where similar genes have been successfully isolated from other plants. Comparative bioinformatic analysis of the nucleotide sequences obtained from transcriptome were carried out using NCBI BLAST, BLASTP, RPS-BLAST, BLASTX and PSI-BLAST to identify homologues of the related genes and for the proper identification of gene. Nucleotide sequence alignments were performed through clustalW version 1.82 whenever multiple sequences were found from the "gene pool". The alignment was then edited. Gene specific primers (both forward and reverse) were selected manually or through Primer 3 plus tool and the primers were custom synthesized.

All oligonucleotides used in this study were synthesized and HPLC purified by the supplier and procured from Integrated DNA Technologies (IDT). Stock solution of about 100 pmol were prepared in autoclaved ddH2O and stored at about −20° C., in aliquots for use.

| Oligouueltotides Sequeuees used as primers forPCR | | | |
|---|---|---|---|
| Primer name | SEQ ID NO | Oligonucleotide sequence | Amplified product from cDNA |
| COLHLZ F | 1 | TCTTGCTCGCTACCAACATT | 883 |
| COLHLZ R | 1 | GCACTGTTCCTATGGCCTCA | |
| COLHLZ F | 4 | ACCCATTTCCTTGTTTCCTCCTT | 926 |
| COLHLZ R | 4 | GCACTGTTCCTATGGCCTCAT | |

Example 2 Amplification, Cloning and Sequencing of Homeobox-Leucine Zipper HAT22 from C. olitorius and C. capsularis Total RNA was isolated from three days old seedlings grown on MS medium as previously described by Chomczynski P and Sacchi N, Single-step method of RNA isolation by acid guanidinium thio cyanate-phenol-chloro form extraction. (Anal Biochem 1987, 162: 156-159). The quality or the integrity of the RNA was checked by agarose gel electrophoresis and was quantified using Thermo Scientific Nano Drop 2000 as per standard procedures. cDNA first strand was synthesised using SuperScript III reverse transcriptase (Invitrogen) following the manufacturer's instructions. The gene was amplified from the cDNA by PCR using the gene specific primers. The PCR reaction (504) contained 1 μL of cDNA, 20 pmoles of each primers, 5 μL of 10×PCR Buffer, 5 μL of 2.5 mM dNTP mix and 1.0 unit of PfuTaq DNA polymerase. PCR was carried out in Thermal Cycler (Applied Biosystems) using the following conditions: initial denaturation for about 5 min at approximately 95° C. followed by 35 cycles of denaturation at approximately 95° C. for about 30 sec, annealing at approximately 58° C. for about 30 sec and extension at approximately 72° C. for about 1 min, with a final extension at approximately 72° C. for about 7 min. The PCR product was analyzed by 1% agarose gel using 1×TAE buffer and the amplicon was eluted from the gel using QIAGEN gel extraction kit following the manufacturer's instructions. The purified PCR product was ligated into pCR®8/GW/TOPO® TA cloning kit (Invitrogen) and transformed into competent E. coli cells (Invitrogen). Plasmids were isolated from putative colonies using QIAprip Spin Miniprep Kit (QIAGEN) following the manufacturerays old seedlings grown on MS medium as previously described by Choe gene specific primers and positive plasmids were subjected to Sequencing.

Example 3 Analysis of the Sequence

The nucleotide sequence and the amino acid sequence were analyzed by BLASTN and BLASTP programs respectively. The sequences reported from other plants were aligned with ClustalW. Phylogenetic analysis was carried out using the Neighbour Joining (NJ).

Example 4 Pathway Construction of Fiber Biosynthesis

Automatic metabolic pathway reconstruction showcasing role of homeobox-leucine zipper HAT22 in fiber biosynthesis was constructed by identifying orthologs from C. olitorus and C. capsularis predicted protein compared with Arbidopsis genome. Homeobox-leucine zipper HAT22 catalyzed enzymatic reactions encoded within C. olitorus and C. capsularis genome were constructed using enzymatic reactions available in Resnet-Plant 3.0 database for Pathway Studio as well as from metabolic pathway databases.

INCORPORATION BY REFERENCE

All of the U.S. patents, U.S. published patent applications, and published PCT applications that cited herein are hereby incorporated by reference.

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed.

```
LENGTH: 1296 bp
TYPE: DNA
FEATURE NAME/KEY: Intron, exon including 150 bp 5' UTR and 150 bp 3' UTR
ORGANISM: Jute, C. olitorius
                                                                SEQ ID NO: 1
CACCCCCCTAATTAACACTCCTTCCTCTCATTTCCTCTCTAAGAATTTTTTTTAAAAAAAATTACAACCCTTTT

CCTTGTTTCCTCCTTAGCATCAACATTTTCTTGCTCGCTACCAACATTTTCTCAGGTTTGAAGTTTGAAACTACC

ATGGGTTTTGATGATATTTGTAACACTGGCCTTGGTCTTGGACTAGGCTGCCTTGTGAAGCAAGAAAAGTATTCG

CAGTCTGATCATCAGCAGCAAAAGAAGAAGAAATTGTTCTTGAAAGATGATCAGTTTTTCCCATCTCTTACTTTA

GGTCCATCAGATGACATATACCAATTATCTCCTGCTAATAAAATTCATGGGGAATCAACTGATTTGCACCAACAA

CAACAAGCCTCTTCTATAAGTGGAGTATCTTCATTTTCTAACTCTAGTGTCAAGAAGGAGAAAGATATTTGTGGT

GAAGAGGTAGAATTGGAAAGAATGTCTTCAAGGGTCAGTGATGAAGATGATGAAGGCAGCCCCAGGAAGAAACTT

CGGCTTAGCAAAGAACAAGCTGCCATTTTAGAAGACAGCTTCAAAGAACACAGCACTCTCAATCCTGTAAATCAT

CTTCCCTTGTCCTTTTAATATGTTATTTCATGTTTTATATACAATTTTATTGCATATAATCTTAATATTTACTTG

TTTCTATTGTTAACAGAAACAGAAGCAGGCTTTAGCAGAACATCTGAATCTTAGGCCACGGCAAGTGGAAGTATG

GTTCCAAAACAGGAGAGCCAGGTTAATTTTCCTTTCAATTTTGACCCTATATTCATAGCTTGGCCTTATATGAGT

TTATTCCCTTACTTTGGATTCTCTTTTTGAAACAACAGGACAAAGCTGAAACAGACTGAAGTAGATTGTGAGTTA

CTGAAGAAATGTTGTGAGACATTAACAGAAGAGAACAAACGGTTGCAGAAGGAACTGCAGGAGCTTAAATCATTG

AAATTGACAGCATCTTATTATATGCAGCTGCCGGCGGCCACCCTCACCATGTGCCCTTCCTGTGAGAGGGTTGCC

GGCGCCGGTGAAGGTCCTTCCAGTACAAGCCCTTTTACAATTGGACAGAAATCTCACTTCTTCAACCCCTTCACT

CACCCATCTGCAGCATGCTAGGCAACTTGTTGATGAGGCCATAGGAACAGTGCTATATTTTGTTCTAGGCTTTA

TTTATGTATGTCAAAATTATATATATGATCAGTATGGAGTAATTAAATCTTAAAGTATAAGTAGGCTAATATCTT

TATATTTCTTGTATAAATTAA

LENGTH: 804 bp
TYPE: DNA
ORGANISM: Jute, C. olitorius
FEATURE NAME/KEY: CDS
LOCATION: (1) . . . (804)
                                                                SEQ ID NO: 2
ATGGGTTTTGATGATATTTGTAACACTGGCCTTGGTCTTGGACTAGGCTGCCTTGTGAAGCAAGAAAAGTATTCG

CAGTCTGATCATCAGCAGCAAAAGAAGAAGAAATTGTTCTTGAAAGATGATCAGTTTTTCCCATCTCTTACTTTA

GGTCCATCAGATGACATATACCAATTATCTCCTGCTAATAAAATTCATGGGGAATCAACTGATTTGCACCAACAA

CAACAAGCCTCTTCTATAAGTGGAGTATCTTCATTTTCTAACTCTAGTGTCAAGAAGGAGAAAGATATTTGTGGT

GAAGAGGTAGAATTGGAAAGAATGTCTTCAAGGGTCAGTGATGAAGATGATGAAGGCAGCCCCAGGAAGAAACTT

CGGCTTAGCAAAGAACAAGCTGCCATTTTAGAAGACAGCTTCAAAGAACACAGCACTCTCAATCCTAAACAGAAG

CAGGCTTTAGCAGAACATCTGAATCTTAGGCCACGGCAAGTGGAAGTATGGTTCCAAAACAGGAGAGCCAGGACA

AAGCTGAAACAGACTGAAGTAGATTGTGAGTTACTGAAGAAATGTTGTGAGACATTAACAGAAGAGAACAAACGG

TTGCAGAAGGAACTGCAGGAGCTTAAATCATTGAAATTGACAGCATCTTATTATATGCAGCTGCCGGCGGCCACC

CTCACCATGTGCCCTTCCTGTGAGAGGGTTGCCGGCGCCGGTGAAGGTCCTTCCAGTACAAGCCCTTTTACAATT

GGACAGAAATCTCACTTCTTCAACCCCTTCACTCACCCATCTGCAGCATGCTAG
```

LENGTH: 267
TYPE: PRT
ORGANISM: Jute, *C. olitorius*

SEQ ID NO: 3

MGFDDICNTGLGLGLGCLVKQEKYSQSDHQQQKKKKLFLKDDQFFPSLTLGPSDDIYQL-
SPANKIHGESTDLHQQQQASSISG

VSSFSNSSVKKEKDICGEEVELERMSSRVSDEDDEGSPRKKLRLSKEQAAILEDSFKEH-
STLNPKQKQALAEHLNLRPRQVEV

WFQNRRARTKLKQTEVDCELLKKCCETLTEENKRLQKELQELKSLKLTASYYMQL-
PAATLTMCPSCERVAGAGEGPSSTSPFT

IGQKSHFFNPFTHPSAAC

LENGTH: 1337 bp
TYPE: DNA
FEATURE NAME/KEY: Intron, exon including 150 bp 5' UTR and 150 bp 3' UTR
ORGANISM: Jute, *C. capsularis*

SEQ ID NO: 4

CTCAAACAAGTTCCTAATTAACACTCCTTCCTCTCATTTCCTCTCTAAGAAAAAAAAAATACAACCCATTTCCTT

GTTTCCTCCTTAGCATCAAGATTAATTTTCTTGCTAGCTACCAACATTTTTCTAGGTTTGAAGTTTGAAACTACC

ATGGGTTTTGATGATATTTGTAACACTGGCCTTAATCTTGGACTCGGATGCCTTGTGAAGCAAGAAAAGTATTCG

CCGTCCGATCATCAGCAGCAAAAGAAGAAGAAATTGTTGTTGAAAGATGATCAGTTTTTCCCATCTCTTACTTTA

GGTCCATCAGATGACATATACCAATTATCTGCTGCTAATAAATTAGCTCATGGGGAATCAATTGATTTGCACCAA

CAACAACAAGCCTCTTCTATCAGTGGAGTATCTTCATTTTCTAACTCTAGTGTCAAGAAGGAGAAAGATATTTGT

GGTGAAGAGGTAGAATTGGAGAGAATGTCTTCAAGGGTCAGTGATGAAGATGATGAAGGCAGCCCCAGGAAGAAA

CTTCGGCTTAGCAAAGAACAAGCTGCCATTTTAGAAGACAGCTTCAAAGAACACAGCACTCTCAATCCTGTAAAT

CATCTTCTAATTAATTCCCTTGTCTTTTTCTATATCATTTCATGTTTTATATTAATTTTATTGCACATAATCTTA

ATATTTACTTGTTTCTCATGTTAACAGAAACAGAAGCAGGCTTTAGCAGAACATCTGAATCTTAGGCCACGGCAA

GTGGAAGTATGGTTCCAAAACAGGAGAGCCAGGTTAATTTTCCTTTCAATTTTGACCATATATTATATACATAGC

TTGGCCTTGTATGATTTTATATTATTCTCTTACTTTGGATTCTCTTTTTGAAACAACAGGACAAAGCTGAAACAG

ACTGAAGTAGATTGTGAGTTACTGAAGAAATGTTGTGAGACATTAACAGAAGAGAACAAACGGTTGCAGAAGGAA

CTGCAGGAGCTTAAATCATTGAAATTGACAACATCTTATTATATGCAGCTGCCGGCTGCCACCCTCACCATGTGC

CCTTCCTGTGAGAGGGTTGCCGGCACCGGTGAAGGCCCTTCCAGTACAAGCCCTTTTACAATTGGACAGAAATCT

CACTTCTTCAACCCCTTCACTCACCCATCAGCCGCATGCTAGGCAACTTGTTGATGAGGCCATAGGAACAGTGCT

ATTTTTGTTCTAGGCTTTTTATTTATGTCAAATATATATATGATCAGTATGGAGTAATTAAATCCTGAAGTATTA

TAAGTAGGCTAATATCTTTATATTTCTTGTATAAATTAAGAT

LENGTH: 807
TYPE: DNA
ORGANISM: Jute, *C. capsularis*
FEATURE NAME/KEY: CDS
LOCATION: (1) . . . (807)

SEQ ID NO: 5

ATGGGTTTTGATGATATTTGTAACACTGGCCTTAATCTTGGACTCGGATGCCTTGT-
GAAGCAAGAAAAGTATTCGCCGTCCGA

TCATCAGCAGCAAAAGAAGAAGAAATTGTTGTTGAAAGATGATCAGTTTTTCCCATCTCT-
TACTTTAGGTCCATCAGATGACA

TATACCAATTATCTGCTGCTAATAAATTAGCTCATGGGGAATCAATTGATTTGCAC-
CAACAACAACAAGCCTCTTCTATCAGT

GGAGTATCTTCATTTTCTAACTCTAGTGTCAAGAAGGAGAAAGATATTTGTGGTGAAGAG-
GTAGAATTGGAGAGAATGTCTTC

AAGGGTCAGTGATGAAGATGATGAAGGCAGCCCCAGGAAGAAACTTCGGCTTAG-
CAAAGAACAAGCTGCCATTTTAGAAGACA

GCTTCAAAGAACACAGCACTCTCAATCCTAAACAGAAGCAGGCTTTAGCAGAACATCT-
GAATCTTAGGCCACGGCAAGTGGAA

-continued

GTATGGTTCCAAAACAGGAGAGCCAGGACAAAGCTGAAACAGACTGAAGTAGATTGT-
GAGTTACTGAAGAAATGTTGTGAGAC

ATTAACAGAAGAGAACAAACGGTTGCAGAAGGAACTGCAGGAGCTTAAATCATTGAAATT-
GACAACATCTTATTATATGCAGC

TGCCGGCTGCCACCCTCACCATGTGCCCTTCCTGTGAGAGGGTTGCCGGCACCGGT-
GAAGGCCCTTCCAGTACAAGCCCTTTT

ACAATTGGACAGAAATCTCACTTCTTCAACCCCTTCACTCACCCATCAGCCGCATGCTAG

LENGTH: 268
TYPE: PRT
ORGANISM: Jute, C. capsularis

SEQ ID NO: 6

MGFDDICNTGLNLGLGCLVKQEKYSPSDHQQQKKKKLLLKDDQFFPSLTLGPSDDIYQL-
SAANKLAHGESIDLHQQQQASSIS

GVSSFSNSSVKKEKDICGEEVELERMSSRVSDEDDEGSPRKKLRLSKEQAAILEDSFKEH-
STLNPKQKQALAEHLNLRPRQVE

VWFQNRRARTKLKQTEVDCELLKKCCETLTEENKRLQKELQELKSLKLTTSYYMQL-
PAATLTMCPSCERVAGTGEGPSSTSPF

TIGQKSHFFNPFTHPSAAC

---

What is claimed is:

1. A polynucleotide comprising a cDNA having at least 95% sequence identity to the nucleotide sequence set forth in SEQ ID NO: 2 or 5, wherein said polynucleotide encodes a homeobox-leucine zipper HAT22 protein.

2. The polynucleotide according to claim 1, wherein the cDNA has at least 98% sequence identity to the nucleotide sequence set forth in SEQ ID NO: 2.

3. The polynucleotide according to claim 1, wherein the cDNA has at least 98% sequence identity to the nucleotide sequence set forth in SEQ ID NO: 5.

4. A recombinant gene construct comprising the polynucleotide of claim 1, wherein the polynucleotide is expressible in a host cell to produce a homeobox-leucine zipper HAT22 polypeptide in *Corchorus olitorius* and *Corchorus capsularis*.

5. The recombinant gene construct according to claim 4, further comprising a promoter region operably-linked to a nucleic acid molecule set forth in a) or b), wherein said promoter enhances the transcription or expression of the polynucleotide.

6. A transformant comprising the recombinant gene construct of claim 4, wherein said transformant is capable of expressing the polynucleotide, and said transformant produces a homeobox-leucine zipper HAT22 polypeptide.

7. A method for producing a transgenic plant, the method comprising the steps of:
   a) introducing into a plant cell the recombinant gene construct of claim 4;
   b) expressing a polypeptide having at least 95% sequence identity to the amino acid sequence set forth in SEQ ID NO: 3 or SEQ ID NO: 6; and c) cultivating the plant cell under conditions for promoting plant growth and development.

8. The method of claim 7, wherein said polypeptide has: at least 98% sequence identity to said amino acid sequence.

9. The method of claim 7, wherein said polypeptide has: at least 99% sequence identity to said amino acid sequence.

10. An expression construct comprising the polynucleotide of claim 1, wherein the polynucleotide is operatively associated with a regulatory nucleic acid molecule containing transcriptional or translational regulatory signals, or both, that controls expression of the polynucleotide in a host cell.

11. A material isolated from the transformant of claim 6, wherein said material comprises the polynucleotide.

12. A seed from the transformant of claim 6, wherein said seed comprises the polynucleotide.

13. A method of inducing, initiating, improving, or enhancing plant fiber growth and plant height in a jute plant, comprising incorporating in to a jute plant the isolated polynucleotide of claim 1.

14. The polynucleotide of claim 1, wherein said cDNA has 100% sequence identity to said nucleotide sequence.

15. The method of claim 7, wherein said polypeptide has 100% sequence identity to said amino acid sequence.

* * * * *

SEQUENCE LISTING

<160> NUMBER OF SEQ ID NOS: 10

<210> SEQ ID NO 1
<211> LENGTH: 1296
<212> TYPE: DNA
<213> ORGANISM: Corchorus olitorius

<400> SEQUENCE: 1

| | | | | |
|---|---|---|---|---|
| cacccccta | attaacactc | cttcctctca | tttcctctct | aagaattttt ttttaaaaaa | 60 |
| aattacaacc | cttttccttg | tttcctcctt | agcatcaaca | ttttcttgct cgctaccaac | 120 |
| attttctcag | gtttgaagtt | tgaaactacc | atgggttttg | atgatatttg taacactggc | 180 |
| cttggtcttg | gactaggctg | ccttgtgaag | caagaaaagt | attcgcagtc tgatcatcag | 240 |
| cagcaaaaga | agaagaaatt | gttcttgaaa | gatgatcagt | ttttcccatc tcttacttta | 300 |
| ggtccatcag | atgacatata | ccaattatct | cctgctaata | aaattcatgg ggaatcaact | 360 |
| gatttgcacc | aacaacaaca | agcctcttct | ataagtggag | tatcttcatt ttctaactct | 420 |
| agtgtcaaga | aggagaaaga | tatttgtggt | gaagaggtag | aattggaaag aatgtcttca | 480 |
| agggtcagtg | atgaagatga | tgaaggcagc | cccaggaaga | aacttcggct tagcaaagaa | 540 |
| caagctgcca | ttttagaaga | cagcttcaaa | gaacacagca | ctctcaatcc tgtaaatcat | 600 |
| cttcccttgt | ccttttaata | tgttatttca | tgttttatat | acaatttat tgcatataat | 660 |
| cttaatattt | acttgtttct | attgttaaca | gaaacagaag | caggctttag cagaacatct | 720 |
| gaatcttagg | ccacggcaag | tggaagtatg | gttccaaaac | aggagagcca ggttaatttt | 780 |
| cctttcaatt | ttgaccctat | attcatagct | tggccttata | tgagtttatt ccttactttt | 840 |
| ggattctctt | tttgaaacaa | caggacaaag | ctgaaacaga | ctgaagtaga ttgtgagtta | 900 |
| ctgaagaaat | gttgtgagac | attaacgaaa | gagaacaaac | ggttgcagaa ggaactgcag | 960 |
| gagcttaaat | cattgaaatt | gacagcatct | tattatatgc | agctgccggc ggccaccctc | 1020 |
| accatgtgcc | cttcctgtga | gagggttgcc | ggcgccggtg | aaggtccttc cagtacaagc | 1080 |
| ccttttacaa | ttggacagaa | atctcacttc | ttcaaccct | tcactcaccc atctgcagca | 1140 |
| tgctaggcaa | cttgttgatg | aggccatagg | aacagtgcta | tattttgtt ctaggcttta | 1200 |
| tttatgtatg | tcaaaattat | atatatgatc | agtatggagt | aattaaatct taaagtataa | 1260 |

```
gtaggctaat atctttatat ttcttgtata aattaa                              1296
```

<210> SEQ ID NO 2
<211> LENGTH: 804
<212> TYPE: DNA
<213> ORGANISM: Corchorus olitorius

<400> SEQUENCE: 2

```
atgggttttg atgatatttg taacactggc cttggtcttg gactaggctg ccttgtgaag    60
caagaaaagt attcgcagtc tgatcatcag cagcaaaaga agaagaaatt gttcttgaaa   120
gatgatcagt ttttcccatc tcttacttta ggtccatcag atgacatata ccaattatct   180
cctgctaata aaattcatgg ggaatcaact gatttgcacc aacaacaaca agcctcttct   240
ataagtggag tatcttcatt ttctaactct agtgtcaaga aggagaaaga tatttgtggt   300
gaagaggtag aattggaaag aatgtcttca agggtcagtg atgaagatga tgaaggcagc   360
cccaggaaga aacttcggct tagcaaagaa caagctgcca ttttagaaga cagcttcaaa   420
gaacacagca ctctcaatcc taaacagaag caggctttag cagaacatct gaatcttagg   480
ccacggcaag tggaagtatg gttccaaaac aggagagcca ggacaaagct gaaacagact   540
gaagtagatt gtgagttact gaagaaatgt tgtgagacat aacagaagaa gaacaaacgg   600
ttgcagaagg aactgcagga gcttaaatca ttgaaattga cagcatctta ttatatgcag   660
ctgccggcgg ccacccctca catgtgccct tcctgtgaga gggttgccgg cgccggtgaa   720
ggtccttcca gtacaagccc ttttacaatt ggacagaaat ctcacttctt caaccccttc   780
actcacccat ctgcagcatg ctag                                          804
```

<210> SEQ ID NO 3
<211> LENGTH: 267
<212> TYPE: PRT
<213> ORGANISM: Corchorus olitorius

<400> SEQUENCE: 3

```
Met Gly Phe Asp Asp Ile Cys Asn Thr Gly Leu Gly Leu Gly Leu Gly
1               5                   10                  15

Cys Leu Val Lys Gln Glu Lys Tyr Ser Gln Ser Asp His Gln Gln Gln
            20                  25                  30

Lys Lys Lys Lys Leu Phe Leu Lys Asp Asp Gln Phe Phe Pro Ser Leu
        35                  40                  45

Thr Leu Gly Pro Ser Asp Asp Ile Tyr Gln Leu Ser Pro Ala Asn Lys
    50                  55                  60

Ile His Gly Glu Ser Thr Asp Leu His Gln Gln Gln Ala Ser Ser
65                  70                  75                  80

Ile Ser Gly Val Ser Ser Phe Ser Asn Ser Ser Val Lys Lys Glu Lys
                85                  90                  95

Asp Ile Cys Gly Glu Glu Val Glu Leu Glu Arg Met Ser Ser Arg Val
            100                 105                 110

Ser Asp Glu Asp Asp Glu Gly Ser Pro Arg Lys Lys Leu Arg Leu Ser
        115                 120                 125

Lys Glu Gln Ala Ala Ile Leu Glu Asp Ser Phe Lys Glu His Ser Thr
    130                 135                 140

Leu Asn Pro Lys Gln Lys Gln Ala Leu Ala Glu His Leu Asn Leu Arg
145                 150                 155                 160

Pro Arg Gln Val Glu Val Trp Phe Gln Asn Arg Arg Ala Arg Thr Lys
                165                 170                 175
```

Leu Lys Gln Thr Glu Val Asp Cys Glu Leu Leu Lys Lys Cys Cys Glu
            180                 185                 190

Thr Leu Thr Glu Glu Asn Lys Arg Leu Gln Lys Glu Leu Gln Glu Leu
        195                 200                 205

Lys Ser Leu Lys Leu Thr Ala Ser Tyr Tyr Met Gln Leu Pro Ala Ala
    210                 215                 220

Thr Leu Thr Met Cys Pro Ser Cys Glu Arg Val Ala Gly Ala Gly Glu
225                 230                 235                 240

Gly Pro Ser Ser Thr Ser Pro Phe Thr Ile Gly Gln Lys Ser His Phe
                245                 250                 255

Phe Asn Pro Phe Thr His Pro Ser Ala Ala Cys
            260                 265

<210> SEQ ID NO 4
<211> LENGTH: 1317
<212> TYPE: DNA
<213> ORGANISM: Corchorus capsularis

<400> SEQUENCE: 4
ctcaaacaag ttcctaatta acactccttc ctctcatttc ctctctaaga aaaaaaaat       60
acaaccccatt tccttgtttc ctccttagca tcaagattaa ttttcttgct agctaccaac    120
attttctag gtttgaagtt tgaaactacc atgggttttg atgatatttg taacactggc      180
cttaatcttg gactcggatg ccttgtgaag caagaaaagt attcgccgtc cgatcatcag     240
cagcaaaaga gaagaaatt gttgttaaaa gatgatcagt ttttcccatc tcttacttta     300
ggtccatcag atgacatata ccaattatct gctgctaata aattagctca tggggaatca    360
attgattgc accaacaaca caagcctct tctatcagtg gagtatcttc attttctaac      420
tctagtgtca agaaggagaa agatatttgt ggtgaagagg tagaattgga gagaatgtct     480
tcaagggtca gtgatgaaga tgatgaaggc agccccagga gaaacttcg gcttagcaaa    540
gaacaagctg ccatttttaga agacagcttc aaagaacaca gcactctcaa tcctgtaaat   600
catcttctaa ttaattccct tgtctttttc tatatcattt catgttttat attaattttta   660
ttgcacataa tcttaatatt tacttgtttc tcatgttaac agaaacagaa gcaggctttta  720
gcagaacatc tgaatcttag gccacggcaa gtggaagtat ggttccaaaa caggagagcc   780
aggttaattt tcctttcaat tttgaccata ttatatac atagcttggc cttgtatgat      840
tttatattat tctcttactt tggattctct ttttgaaaca acaggacaaa gctgaaacag   900
actgaagtag attgtgagtt actgaagaaa tgttgtgaga cattaacaga agagaacaaa   960
cggttgcaga aggaactgca ggagcttaaa tcattgaaat tgacaacatc ttattatatg 1020
cagctgccgg ctgccaccct caccatgtgc ccttcctgtg agagggttgc cggcaccggt 1080
gaaggccctt ccagtacaag cccttttaca attggacaga aatctcactt cttcaacccc 1140
ttcactcacc catcagccgc atgctaggca acttgttgat gaggccatag aacagtgct  1200
atttttgttc taggcttttt atttatgtca aatatatata tgatcagtat ggagtaatta 1260
aatcctgaag tattataagt aggctaatat ctttatattt cttgtataaa ttaagat    1317

<210> SEQ ID NO 5
<211> LENGTH: 807
<212> TYPE: DNA
<213> ORGANISM: Corchorus capsularis

<400> SEQUENCE: 5

```
atgggttttg atgatatttg taacactggc cttaatcttg gactcggatg ccttgtgaag    60
caagaaaagt attcgccgtc cgatcatcag cagcaaaaga agaagaaatt gttgttgaaa   120
gatgatcagt ttttcccatc tcttacttta ggtccatcag atgacatata ccaattatct   180
gctgctaata aattagctca tggggaatca attgatttgc accaacaaca acaagcctct   240
tctatcagtg gagtatcttc attttctaac tctagtgtca agaaggagaa agatatttgt   300
ggtgaagagg tagaattgga gagaatgtct tcaagggtca gtgatgaaga tgatgaaggc   360
agccccagga agaaacttcg gcttagcaaa gaacaagctg ccattttaga agacagcttc   420
aaagaacaca gcactctcaa tcctaaacag aagcaggctt tagcagaaca tctgaatctt   480
aggccacggc aagtggaagt atggttccaa acaggagag ccaggacaaa gctgaaacag   540
actgaagtag attgtgagtt actgaagaaa tgttgtgaga cattaacaga agagaacaaa   600
cggttgcaga aggaactgca ggagcttaaa tcattgaaat tgacaacatc ttattatatg   660
cagctgccgg ctgccaccct caccatgtgc ccttcctgtg agagggttgc cggcaccggt   720
gaaggcccctt ccagtacaag ccctttaca attggacaga aatctcactt cttcaacccc   780
ttcactcacc catcagccgc atgctag                                      807
```

<210> SEQ ID NO 6
<211> LENGTH: 268
<212> TYPE: PRT
<213> ORGANISM: Corchorus capsularis

<400> SEQUENCE: 6

```
Met Gly Phe Asp Asp Ile Cys Asn Thr Gly Leu Asn Leu Gly Leu Gly
1               5                   10                  15

Cys Leu Val Lys Gln Glu Lys Tyr Ser Pro Ser Asp His Gln Gln Gln
            20                  25                  30

Lys Lys Lys Lys Leu Leu Leu Lys Asp Asp Gln Phe Phe Pro Ser Leu
        35                  40                  45

Thr Leu Gly Pro Ser Asp Asp Ile Tyr Gln Leu Ser Ala Ala Asn Lys
    50                  55                  60

Leu Ala His Gly Glu Ser Ile Asp Leu His Gln Gln Gln Gln Ala Ser
65                  70                  75                  80

Ser Ile Ser Gly Val Ser Ser Phe Ser Asn Ser Ser Val Lys Lys Glu
                85                  90                  95

Lys Asp Ile Cys Gly Glu Glu Val Glu Leu Glu Arg Met Ser Ser Arg
            100                 105                 110

Val Ser Asp Glu Asp Asp Glu Gly Ser Pro Arg Lys Lys Leu Arg Leu
        115                 120                 125

Ser Lys Glu Gln Ala Ala Ile Leu Glu Asp Ser Phe Lys Glu His Ser
    130                 135                 140

Thr Leu Asn Pro Lys Gln Lys Gln Ala Leu Ala Glu His Leu Asn Leu
145                 150                 155                 160

Arg Pro Arg Gln Val Glu Val Trp Phe Gln Asn Arg Arg Ala Arg Thr
                165                 170                 175

Lys Leu Lys Gln Thr Glu Val Asp Cys Glu Leu Leu Lys Lys Cys Cys
            180                 185                 190

Glu Thr Leu Thr Glu Glu Asn Lys Arg Leu Gln Lys Glu Leu Gln Glu
        195                 200                 205

Leu Lys Ser Leu Lys Leu Thr Thr Ser Tyr Tyr Met Gln Leu Pro Ala
    210                 215                 220

Ala Thr Leu Thr Met Cys Pro Ser Cys Glu Arg Val Ala Gly Thr Gly
```

-continued

```
               225                 230                 235                 240

Glu Gly Pro Ser Ser Thr Ser Pro Phe Thr Ile Gly Gln Lys Ser His
                245                 250                 255

Phe Phe Asn Pro Phe Thr His Pro Ser Ala Ala Cys
            260                 265

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tcttgctcgc taccaacatt                                             20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcactgttcc tatggcctca                                             20

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acccatttcc ttgtttcctc ctt                                         23

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcactgttcc tatggcctca t                                           21
```